US00PP28816P3

(12) United States Plant Patent

Klemm et al.

(10) Patent No.: US PP28,816 P3

(45) Date of Patent: Dec. 26, 2017

(54) *PELARGONIUM* PLANT NAMED 'KLEPS15377'

(50) Latin Name: *Pelargonium grandiflorum*
Varietal Denomination: KLEPS15377

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 76 days.

(21) Appl. No.: 14/998,946

(22) Filed: Mar. 9, 2016

(65) Prior Publication Data

US 2017/0265360 P1 Sep. 14, 2017

(51) Int. Cl.
*A01H 5/02* (2006.01)

(52) U.S. Cl.
USPC ..... Plt./324

(58) Field of Classification Search
USPC ..... Plt./324
See application file for complete search history.

(56) References Cited

PUBLICATIONS

UPOV hit on *Pelargonium* plant named 'KLEPS 15377', CH PBR 16-3071, application date Jun. 16, 2016.*
UPOV hit on *Pelargonium* plant named 'KLEPS15377', QZ PBR 20161687, application date Jul. 4, 2016.*

* cited by examiner

*Primary Examiner* — Anne M Grunberg
(74) *Attorney, Agent, or Firm* — Barbara Campbell; Bethany R. Roahrig; Cochran Freund & Young, LLC

(57) ABSTRACT

A new *pelargonium* plant particularly distinguished by violet flowers with dark-purple eyes and an upright, round, and bushy habit, is disclosed.

1 Drawing Sheet

Genus and species: *Pelargonium grandiflorum.*
Variety denomination: 'KLEPS15377'.

BACKGROUND OF THE NEW PLANT

The present invention comprises a new and distinct variety of *pelargonium*, botanically known as *Pelargonium grandiflorum* and hereinafter referred to by the variety name 'KLEPS15377'. 'KLEPS15377' originated from a cross-combination in August 2010 in Stuttgart, Germany between the proprietary female *pelargonium* variety 'PSH-2009-C-Violet' (unpatented) and the proprietary male *pelargonium* variety 'PS-2009-0007' (unpatented).

Seeds from the cross-combination in Stuttgart, Germany were obtained. The seeds were sown and plants were grown for evaluation. A single plant was selected in June 2011 and subsequently named 'KLEPS15377'. In August 2011 'KLEPS15377' was first vegetatively propagated by vegetative cuttings from stems and branches. 'KLEPS15377' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Violet flowers with dark-purple eyes; and
2. An upright, round, and bushy habit.

DESCRIPTION OF THE PHOTOGRAPH

This new *pelargonium* plant is illustrated by the accompanying photograph which shows an overall view of the plant. The photograph is of an approximately ten-week-old plant grown in Stuttgart, Germany under greenhouse conditions in April 2014. The colors shown are as true as can be reasonably obtained by conventional photographic procedures.

DESCRIPTION OF THE NEW VARIETY

The following detailed descriptions set forth the distinctive characteristics of 'KLEPS15377'. The data which define these characteristics were collected from asexual reproductions carried out in Stuttgart, Germany. Data was collected on five-month old plants in Stuttgart, Germany under greenhouse conditions in July 2015. Color references are to The R.H.S. Colour Chart of The Royal Horticultural Society of London (R.H.S.), 5$^{th}$ edition (2007).

Classification:
- *Family.*—Geraniaceae.
- *Botanical.*—*Pelargonium grandiflorum.*
- *Common.*—*Pelargonium.*
- *Designation.*—'KLEPS15377'.

Parentage:
- *Female parent.*—The proprietary female *pelargonium* variety 'PSH-2009-C-Violet' (unpatented).
- *Male parent.*—The proprietary male *pelargonium* variety 'PS-2009-0007' (unpatented).

Plant:
- *Form.*—Bushy and round.
- *Habit.*—Upright.
- *Height.*—24.0 cm.
- *Width.*—23.0 cm.
- *Natural flowering season.*—Spring to autumn.

*Propagation type*.—Vegetative cuttings.
*Time to produce a finished flowering plant*.—4 to 5 months.
*Time to initiate and develop roots*.—26 days.
*Root description*.—RHS 27D and fine.

Stems:
*Quantity of stems per plant*.—6.
*Color*.—RHS 137A.
*Surface texture*.—Moderately pubescent.
*Stem form*.—Round.
*Diameter*.—0.7 cm.
*Length*.—6.0 cm to 9.0 cm.
*Internode length*.—1.2 cm to 1.6 cm.
*Anthocyanin*.—Absent.

Leaves:
*Arrangement*.—Alternate.
*Shape*.—Cordate.
*Apex*.—Acute.
*Base*.—Open.
*Margin*.—Crenate.
*Surface texture*.—Upper surface: Smooth to sparsely pubescent. Lower surface: Smooth.
*Length*.—5.0 cm.
*Width*.—6.5 cm.
*Color*.—Upper surface: RHS 137B. Lower surface: RHS 137D.
*Petiole*.—Length: 5.0 cm to 7.0 cm. Diameter: 0.2 cm. Color: RHS 137A. Strength: Medium.
*Venation pattern*.—Palmate.
*Venation color*.—Upper surface: RHS 137D. Lower surface: RHS 138B.

Inflorescence:
*Lastingness of flowers on the plant*.—6 to 10 days.
*Umbels*.—Quantity of umbels per plant: 6. Length: 5.0 cm. Diameter: 5.0 cm.
*Individual florets of the umbel*.—Quantity of florets per umbel: 4 to 6. Depth: 2.0 cm. Diameter: 4.0 cm.
*Fragrance*.—Absent.

Flower buds:
*Cluster shape*.—Round.
*Cluster size*.—Length: 1.0 cm to 1.5 cm. Width: 1.0 cm to 1.8 cm.
*Surface texture*.—Moderately pubescent.
*Bud*.—Height: 0.7 cm to 1.0 cm. Width: 0.5 cm. Shape: Elliptic. Apex: Acute. Base: Obtuse. Margin: Smooth. Color: RHS 137D.

Petals:
*Quantity per flower*.—5 to 6.
*Shape*.—Drop-shaped.
*Apex*.—Round.
*Base*.—Obtuse.
*Margin*.—Entire.
*Length*.—3.5 cm.
*Width*.—2.5 cm.
*Surface texture*.—Upper surface: Smooth. Lower surface: Smooth.
*Color of lobes*.—Upper lobes: Upper surface: RHS N74A (Red-purple) and with RHS N79A (Purple) centers. Lower surface: RHS N74B (Red-purple) and with RHS N79A (Purple) centers. Lower lobes: Upper surface: RHS N74B (Red-purple) with RHS N79C (Purple) centers. Lower surface: RHS N74B (Red-purple) with RHS N79C (Purple) centers.

Petaloids: Absent.

Sepals:
*Number per flower*.—5.
*Shape*.—V-shaped.
*Apex*.—Cuspidate.
*Base*.—Obtuse.
*Margin*.—Entire.
*Surface texture*.—Upper surface: Smooth. Lower surface: Moderately pubescent.
*Color*.—Upper surface: RHS 137D. Lower surface: RHS 137D.
*Length*.—1.1 cm.
*Width*.—0.4 cm.

Pedicel:
*Length*.—2.2 cm.
*Diameter*.—0.1 cm.
*Color*.—RHS 137C.
*Surface texture*.—Moderately pubescent.
*Strength*.—Medium.

Peduncle:
*Length*.—6.0 cm to 7.0 cm.
*Diameter*.—0.2 cm.
*Color*.—RHS 137C.
*Surface texture*.—Moderately pubescent.
*Strength*.—Medium.

Reproductive organs:
*Stamens*.—Quantity of stamens per flower: Greater than 5. Anther length: 0.2 cm. Filament length: 0.6 cm. Filament color: RHS 73A. Pollen amount: Moderate. Pollen color: RHS 72B.
*Pistils*.—Number: 1. Stigma color: RHS N79B. Style length: 1.0 cm. Style color: RHS 72C. Ovary arrangement: Central. Ovary color: RHS 138D. Ovary diameter: 0.1 cm. Ovary length: 0.2 cm.

Fruit and seed set: None observed.

Disease and pest/insect resistance: None observed.

COMPARISON WITH PARENTAL LINES AND KNOWN VARIETY

'KLEPS15377' is distinguished from its parents as described in Table 1:

TABLE 1

Comparison with Parental Lines

| Characteristic | 'KLEPS15377 | Female parent 'PSH-2009-C-Violet' | Male Parent 'PS-2009-0007' |
|---|---|---|---|
| Flower color | Violet with dark-purple eyes | Dark-lavender with dark eyes | Dark-purple with dark eyes |
| Flower size | Medium | Medium | Small |
| Leaf size | Medium | Large | Very small |

'KLEPS15377' can be compared to the commercial variety 'Camvio' (U.S. Plant Pat. No. 20,421), also commercially known as CANDY FLOWERS 'Violet Regal'. Differences between the two varieties are described in Table 2:

TABLE 2

Comparison with Similar Variety

| Characteristic | 'KLEP515377' | Commercial line 'Camvio' |
|---|---|---|
| Flower color | Violet with dark-purple eyes | Dark-violet with dark-red eyes |

We claim:

1. A new and distinct variety of *pelargonium* plant named 'KLEPS15377' as illustrated and described herein.

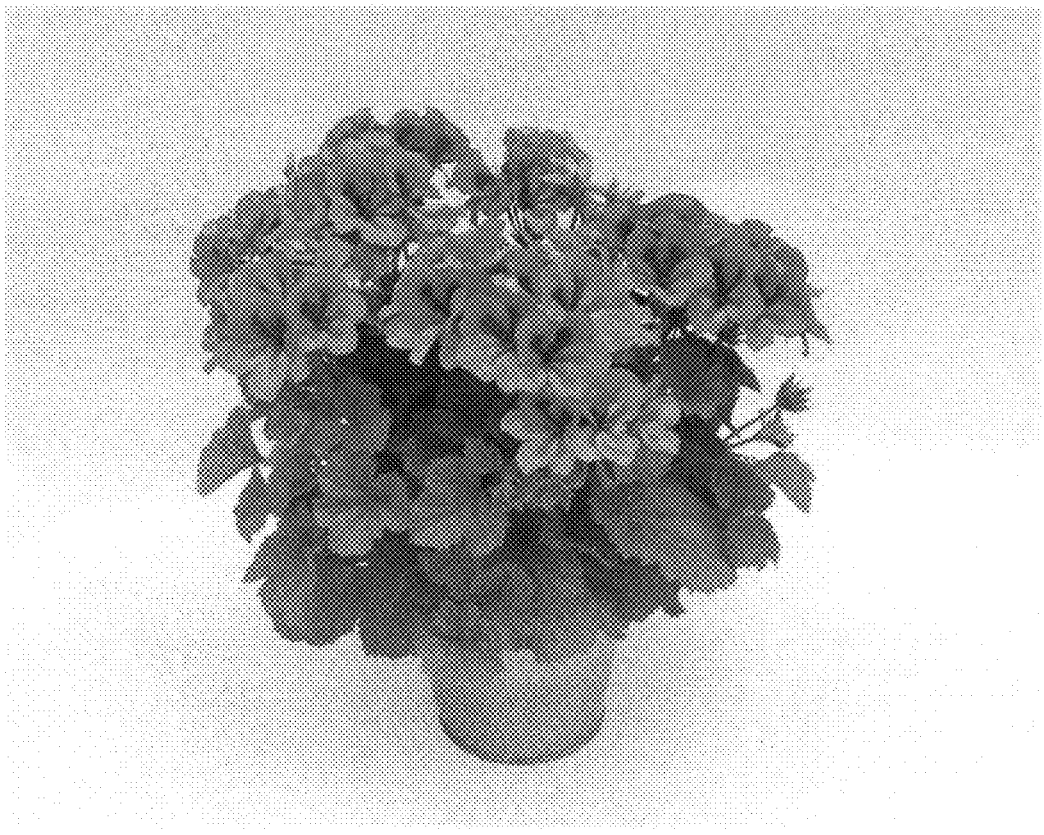

* * * * *